United States Patent [19]

Dabrah et al.

[11] Patent Number: 5,430,055
[45] Date of Patent: Jul. 4, 1995

[54] INHIBITOR OF SQUALENE SYNTHASE

[75] Inventors: Thomas T. Dabrah; H. James Harwood, Jr.; Liang H. Huang; Takushi Kaneko, all of New York, N.Y.

[73] Assignee: Pfizer Inc., New York, N.Y.

[21] Appl. No.: 225,020

[22] Filed: Apr. 8, 1994

[51] Int. Cl.$^6$ ................. A61K 31/34; C07D 307/77
[52] U.S. Cl. ................................... 514/468; 549/235
[58] Field of Search .................... 549/235; 514/468

[56] References Cited

U.S. PATENT DOCUMENTS

| 5,026,554 | 6/1991 | Bartizal et al. | 424/404 |
|---|---|---|---|
| 5,053,425 | 10/1991 | Bartizal et al. | 514/452 |
| 5,055,487 | 10/1991 | Bartizal et al. | 514/452 |
| 5,258,401 | 11/1993 | Berger et al. | 514/452 |

FOREIGN PATENT DOCUMENTS

| 448393 | 9/1991 | European Pat. Off. |
|---|---|---|
| 503520 | 9/1992 | European Pat. Off. |
| 512865 | 11/1992 | European Pat. Off. |
| 522715 | 1/1993 | European Pat. Off. |
| 524671 | 1/1993 | European Pat. Off. |
| 525846 | 2/1993 | European Pat. Off. |
| 568946 | 11/1993 | European Pat. Off. |
| 9212156 | 7/1992 | WIPO |
| 9212157 | 7/1992 | WIPO |
| 9212158 | 7/1992 | WIPO |
| 9212159 | 7/1992 | WIPO |
| 9222660 | 12/1992 | WIPO |
| 9307151 | 4/1993 | WIPO |

OTHER PUBLICATIONS

F. Tamanoi, Trends Biochem. Sci, 18, 349 (1993).
J. B. Gibbs et al, J. Biol. Chem., 268, 7617 (1993).
N. E. Kohl et al, Science, 260, 1934–1937 (1993).
G. L. James et al, Science, 260, 1937–1942 (1993).

Primary Examiner—Cecilia Tsang
Attorney, Agent, or Firm—Peter C. Richardson; Gezina Holtrust; B. Timothy Creagan

[57] ABSTRACT

The culture ATCC 74256 and its mutants are capable of producing zaragozic acid A and other squalene synthase inhibitors.

The compound of formula I herein may be prepared from culture ATCC 74256 and is useful in the treatment of fungal infections, and inhibition of squalene synthase, and protein farnesyltransferase.

2 Claims, No Drawings

INHIBITOR OF SQUALENE SYNTHASE

BACKGROUND OF THE INVENTION

This invention relates to a culture producing zaragozic acid A, and a compound of the formula I below. It also relates to a composition for the treatment of fungal infections and hypercholesterolemia comprising the compound I, and the use of such compound in the treatment of fungal infections, hypercholesterolemia, and in cancer chemotherapy.

The risk of coronary disease may be reduced by lowering the serum cholesterol level. In the biosynthesis of cholesterol, squalene synthase plays a critical role in combining two units of farnesyl diphosphate into squalene which is a penultimate precursor of sterols. Zaragozic acid A, a known squalene synthase inhibitor, also known as squalestatin 1, is reportedly produced by an unidentified culture ATCC 20986, Phoma sp. C2932, *Curvularia lunata*, *Exserohilum rostratum* and *Setosphaeria khartoumensis*. Other known squalene synthase inhibitors are zaragozic acid B and C which are produced by *Sporormiella intermedia* and *Leptodontium elatius*, respectively; squalestatin 2 and 3 are also produced by Phoma sp. C2932.

In cancer chemotherapy, inhibitors of ras farnesylation have been sought, based on the observation that farnesylation is critical for ras protein to localize onto the cytosolic membrane. Interference of the function of mutated ras protein is considered to provide a novel cancer therapy. Zaragozic acid A has been shown to inhibit farnesylation of ras protein. More recently, several peptidominmetic compounds have been disclosed as inhibitors of ras farnesyltransferase.

SUMMARY OF THE INVENTION

The invention provides a novel compound, of use as a squalene synthase inhibitor, an antifungal agent and an inhibitor of protein farnesyltranferase, of the formula

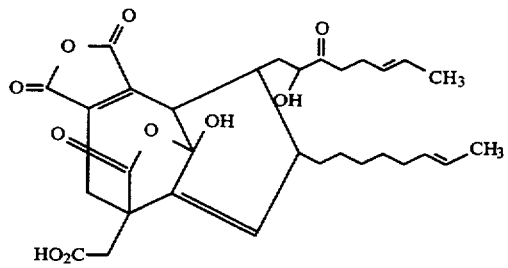

I and the pharmaceutically acceptable acid addition salts thereof.

The compound of formula I contains chiral centers. It is understood that the invention includes the individual diastereomers and enantiomers of the compound of formula I.

The invention also provides a biologically pure culture having all of the identifying characteristics of the unidentified fungus ATCC 74256. In addition, the culture ATCC 74256 and its mutants are capable of producing zaragozic acid A and other known squalene synthase inhibitors.

The invention further provides a composition for the treatment of fungal infections or the inhibition of squalene synthase or farnesyltransferase comprising a compound of formula I in an amount effective in such treatment or inhibition, and a pharmaceutically acceptable carrier.

The invention is also directed to a method for antifungal treatment by administering to a subject in need of such treatment an antifungal amount of a compound of formula I. The invention also relates to a method for (a) the inhibition of squalene synthase or (b) the lowering of the serum cholesterol level by administering to a subject in need of such inhibition or said lowering of said serum cholesterol level an effective amount of a compound of formula I. The invention further relates to a method for the inhibition of protein farnesyltransferase by administering to a subject in need of such inhibition an effective amount of a compound of formula I.

DETAILED DESCRIPTION OF THE INVENTION

The culture of the invention has been deposited in the American Type Culture Collection under accession number ATCC 74256.

The novel culture was isolated from twigs of *Juniperus ashei* Bachh in a Juniper-Scrub Oak forest about 3 miles east of Dripping Springs, Tex., on highway 290.

The culture ATCC 74256 was single-block inoculated from malt extract agar plates onto plates of identification media and the plates were incubated at 25° C. for one week in the dark, and for another three weeks under alternative 13 hours black light (near UV light) and 11 hours darkness. The results were read at varying times but most commonly were taken at 14 days. The colors were determined by comparisons with color chips from Color Standards and Color Nomenclature by Robert Ridgway, 1912.

Identification media used for the characteristics of the strain and references describing their compositions are as follows:

Malt Extract Agar—Raper, K. B. and D. I. Fennell. 1965. The Genus Aspergillus, p. 36.

Oatmeal Agar—ISP #3 medium, Difco.

Potato Dextrose Agar—ATCC medium 336, ATCC Media Handbook, 1984, p. 17.

Cornmeal Agar—Carmichael, J. W. 1957. Mycologia 49: 820–830.

V-8 Juice Agar—ATCC medium 343, ATCC Media Handbook, 1984, p. 17.

Potato Carrot Agar—M. P. Lechevalier, J. Lab. and Clinical Med. 71: 934–944, 1968, but use only 30 g potatoes, 2.5 g carrots and 20 g agar.

Temperature study—Malt extract agar.

Malt Extract Agar—Attaining 1.4 cm diameter in two weeks, deep mouse gray (LI), moderately raised, floccose, smooth, aerial mycelium same as surface; reverse light mouse gray to deep mouse gray (LI); soluble pigment raw sienna to antique brown (III).

Oatmeal Agar—Attaining 3 cm diameter in two weeks, pale pinkish cinnamon, pinkish buff to cinnamon (XXIX), but antique brown to raw umber (III) toward edge, moderately raised, felty, radiately wrinkled, aerial mycelium same as surface; reverse amber brown to argus brown (111); soluble pigment grenadine pink to bittersweet orange (11).

Potato dextrose agar—Attaining 1.1 cm diameter in two weeks, ochraceous-towny (XV) to blackish mouse gray (LI), highly raised, floccose, radiately wrinkled, aerial mycelium ochraceous-tawny (XV); reverse black; soluble pigment tawny (XV) to razel (XIV).

Cornmeal Agar—Attaining 3.1 cm diameter in two weeks, off-white, pale olive-buff to olive-buff (XL), thin to slightly raised, lowly floccose, smooth, aerial mycelium off-white to cream (XVI); reverse colorless to pinard yellow (IV); soluble pigment none to cream (XVI).

V-8 Juice Agar—Attaining 2.1 cm diameter in two weeks, tawny-olive to saccardo's umber but pale pinkish buff to pinkish buff (XXIV) toward edge, moderately raised, floccose, smooth, aerial mycelium same as surface; reverse ochraceous-tawny to cinnamon-brown (XV); soluble pigment yellow ocher to warm buff (XV).

Potato Carrot Agar—Attaining 2.6 cm diameter in two weeks, white to pale olive-gray (LI), slightly raised, floccose, smooth, aerial mycelium white; reverse colorless to pale olive-gray; no soluble pigment.

Morphological Properties—Morphological characteristics were observed 3 weeks after inoculation on malt extract agar: hyphae septate, branched, pale brown to dark brown, 2 to 5 $\mu$m diam. Chlamydospores terminal, lateral or intercalary, single but more often catenulate; globose, subglobose, oval elliptical to elongated; pale brown, brown, to dark brown, 6–20 ($-30$)$\times$4–12 $\mu$m, or 7–12 $\mu$m diam, smooth. No fruiting bodies or condia formed on any of the media used. A slide and a slant of the culture showed pycnidia-like structures. The structures were dark brown to brown-black, globose to subglobose, and measured 190–240 $\mu$m diam., with a long beak which measured 130–660$\times$95–125 $\mu$m. No conidia of any type were observed.

| Temperature Relations - | | | | |
|---|---|---|---|---|
| 20° C. | 28° C. | 37° C. | 45° C. | 50° C. |
| Moderate Growth | Moderate to Good Growth | No Growth | No Growth | No Growth |

The culture ATCC 74256 is characterized by the pink-buff, ochraceous-towny, olive gray to mouse gray aerial mycelium, the brown, gray to black colony reverse, and the slow growth. The efforts to induce spore production failed by using different media, exposing the strain to fluorescent light and black light, or incubating the strain for up to 2 months. The pycnidia-like structures formed at the time of isolation did not produce spores of any type. Thus, the culture is considered to be an unidentified fungus.

Cultivation of the fungal culture of the invention preferably takes place in aqueous nutrient media or on solid media at a temperature of 25° to 30° C., and under stationary aerobic conditions or submerged aerobic conditions with agitation. Nutrient media which are useful for such purposes include a source of assimilable carbon such as sugars, starch and molasses; and a source of organic nitrogen such as casein, enzymatic digest of casein, soybean meal, cottonseed meal, peanut meal and wheat gluten. A source of growth substances such as grain solubles, fish meal and yeast extract as well as salts such as sodium chloride and calcium carbonate and trace minerals such as iron, magnesium, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the organism and throughout its growth.

The compound of formula I of the invention is obtained from the fermentation broth of the fungal culture of the invention, and can be separated therefrom by conventional extraction and chromatographic techniques. For example, the whole fermentation broth may be extracted with ethyl acetate, which is re-extracted with sodium bicarbonate solution, acidified, extracted with ethyl acetate, and concentrated. The crude residue may be dissolved in methanol/water mixtures, and partitioned with an organic solvent such as hexane, toluene or chloroform. The fraction containing the compound is concentrated and then chromatographed. The fractions obtained from chromatography are concentrated to a residue containing about seven components. Each component may be separated by use of semi-preparative high performance liquid chromatography (HPLC).

The pharmaceutically acceptable acid addition salts of compound I are prepared in a conventional manner by treating a solution or suspension of the free acid (I) with about one chemical equivalent of a pharmaceutically acceptable base. Conventional concentration and recrystallization techniques are employed in isolating the salts. Illustrative of suitable bases are alkali metal hydroxides such as sodium or potassium hydroxide, alkaline earth metal hydroxides such as magnesium or calcium hydroxide, and ammonium or organic amines such as diethanolamine or N-methylglucamine.

The compound of formula I and the pharmaceutically acceptable acid addition salts thereof (the active compound) are useful in the treatment of fungal infections, the inhibition of squalene synthase, the lowering of serum cholesterol levels, and the treatment of cancer.

The active compound may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the active compound and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinyl pyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the active compound in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Additionally, the active compound may be administered topically when treating conditions of the skin and this may be done by way of creams, jellies, gels, pastes, and ointments, in accordance with standard pharmaceutical practice.

In general, a therapeutically effective daily dose for the active compound will range from 0.01 to 100 mg/kg, generally from about 1 to about 5 mg/kg, body weight of the subject to be treated for fungal infections and from 0.2 to 100 mg/kg, for instance 0.2 to 1 mg/kg, for the inhibition of squalene synthase and the lowering of the serum cholesterol level. As is generally known, the effective dosage for the active compound depends on the intended route of administration and other factors such as age and weight of the patient, as generally known to a physician. The dosage also depends on the illness to be treated.

The following Examples illustrate the invention.

Example 1

A vial of the culture ATCC 74256 stored at −80° C. was thawed and inoculated into 10 ml seed medium KF, set out in Table 1, in a shake tube. The shake tube was shaken at 28° C. for 48 hours. A 0.6 ml or 1 ml sample of the growth from the shake tube was inoculated into 50 ml of the seed medium KF, and the flasks were incubated on a shaker at 200 rpm for 3 days at 28° C. A 0.6 ml sample of the seed broth was inoculated into 50 ml each of GSC, SP and M media (Tables 2–4), and the flasks were incubated at 28° C. on a shaker (200 rpm) for 4 to 14 days. 2 ml of seed inoculum was used per flask of rice medium (Table 5); a total of 61 flasks were incubated statically at 25° C. in an incubator for 14 to 23 days with 85% humidity.

To scale up, a vial of the strain stored at −80° C. was thawed and inoculated into a tube containing 10 ml of KF seed medium. The tube was shaken at 28 o C for 72 to 96 hours and inoculated into a side arm shake flask containing about 60 ml of KF medium. This side arm shake flask was shaken at 28° C. for 72 hours and inoculated into a bench-top fermentor containing 12 liters of sterile SP medium. The fermentation was run for 168 hours at 28° C. with 8 liters of sterile air/min at 350 rpm.

TABLE 1

| KF Seed Medium* | | |
| --- | --- | --- |
| Corn steep liquor | 5 | g/L |
| Tomato paste | 40 | g |
| Oat flour | 10 | g |
| Glucose | 10 | g |
| Trace element mix+ | 10 | ml |
| (pH adjusted to 6.8) | | |
| +Trace element mix: | | |
| FeSO$_4$.7H$_2$O | 1.0 | g |
| MnSO$_4$.4H$_2$O | 1.0 | g |
| CuCl$_2$.2H$_2$O | 0.025 | g |
| CaCl$_2$.2H$_2$O | 0.1 | g |
| H$_3$BO$_3$ | 0.056 | g |

TABLE 1-continued

| KF Seed Medium* | |
| --- | --- |
| (NH$_4$)$_6$Mo$_7$O$_{24}$.4H$_2$O | 0.019 g |
| ZnSO$_4$.7H$_2$O | 0.2 g |
| Dillsolved in 1 L 0.6 N HCl | |

*U.S. Pat. No. 5,055,487

TABLE 2

| GSC Medium* | |
| --- | --- |
| Glucose | 2% |
| Soluble starch | 2% |
| Corn steep liquor | 2% |
| Peanut powder | 0.5% |
| Peptone | 0.5% |
| Dried yeast | 0.5% |
| CaCO$_3$ | 0.2% |
| Water | 1 L |
| (pH adjusted to 6.5) | |

*J. Antibiot. 41, (9): 1163 (1988)

TABLE 3

| SP Medium* | |
| --- | --- |
| Sugar - Glucose | 20 g |
| Potato deccoction | 200 g |

*J. Antibiot. 44(12): 1467 (1991)

TABLE 4

| M Medium* | |
| --- | --- |
| Malt extract | 3% |
| Water | 1 L |

*J. Basic Microbiol. 31: 69 (1991)

TABLE 5

| Rice Medium* | |
| --- | --- |
| Rice | 50 g |
| Water | 50 ml |

*Mycopathol. 110: 178 (1990)

Assays were done at 4 and 7 days for medium GSC and at 8, 11, and 14 days for medias SP and M.

The antifungal activity of the compound I was determined with a bioassay such as *Cryptococcus bhutanensis* FD 23971. A ten-day-old slant of *C. bhutanensis* was washed with 10 ml of sterile water, and 300 μl of the suspension was mixed with an assay medium consisting of 0.67% of yeast nitrogen based medium (DIFCO) and 0.5% of glucose. 150 ml of the warm medium was poured onto a sterile, polystyrene bioassay plate (245×245×20 mm) and was left to solidify. The solid medium was bored into well-separated wells with a size #2 cork bore, and 25 μl of whole broth or extracted broth was spotted into the wells. The plates were incubated at 28° C. for 2 to 3 days and the zone of inhibition was measured.

The zones of inhibition against *Cryptococcus bhutanensis* on a yeast nitrogen based medium are as follows:

| Compound | Sensitive Strain (against zaragozic Acid A) | Resistant Strain |
| --- | --- | --- |
| Compound of formula I (CP-225,917) | 15 mm | 22 |
| CP-263,114 | 42 | 45 |

Example 2

Squalene Synthase Inhibition Assay

The squalene synthase inhibition assay was conducted in a final volume of 75 μl. The reaction is initiated by addition of 25 μl of the diluted and deoxygenated microsomal suspension to a mixture of 47 μl of the deoxygenated SQS substrate/cofactor solution and 3 μl of the deoxygenated test compound solution as set out in Table 6.

TABLE 6

| Squalene Synthase Assay | |
|---|---|
|  | final assay concentrations |
| Microsomal Protein | 25 μg |
| K$_2$PO$_4$ (pH = 7.4) | 48 mM |
| MgCl$_2$ | 4.8 mM |
| EDTA | 0.33 mM |
| Dithiothreitol | 1.67 mM |
| NaF | 9.50 mM |
| Glucose-6-phosphate Dehydrogenase | 0.95 U |
| NADP+ | 258 uM |
| Glucose-6-phosphate | 2.10 mM |
| DMSO | 4% |
| [1-3H] Farnesyl-pyrophosphate | 5.1 uM |
| Deionized Water | |

The microsomal suspensions were diluted to a microsomal protein concentration of 1 mg/ml and deoxygenated by repetitive cycles of evacuation and airation with nitrogen. Test compound solutions were prepared in dimethyl sulfoxide at concentrations of 25 mM (final assay concentration 1 mM). Control incubations received 3 μl of deoxygenated dimethyl sulfoxide and enzyme blanks received 25 μl of deoxygenated PMED buffer (50 mM K$_2$PO$_4$ (pH=7.4), 5 mM MgCl$_2$, 1 mM EDTA, 5 mM dithiothreitol). Assay tubes were immediately flushed with nitrogen and capped, and the solution was vortexed gently. Following 30 minutes of incubation at 37° C., reactions were terminated by addition of 40 μl of 10M sodium hydroxide. Following reaction termination, 40 μl of absolute ethanol and 10 μl of 2 mg/ml unlabeled squalene in chloroform were added to each tube, the tubes were capped and vortexed vigorously. The mixture was allowed to incubate for 90 minutes at 37° C., after which the mixtures were vortexed and 25 μl aliquots were applied to 1.2×10 cm channels of a silica gel thin layer chromatogram. The chromatogram was developed in toluene: ethyl acetate=9:1. [1-3H]FPP (farnesyl pyrophosphate) remained at the origin whereas the newly formed [3H] squalene migrated with an Rf of 0.74. The region of the chromatogram from 1 cm below the squalene band (visualized with iodine vapors) to the top of the chromatogram was removed and counted in a liquid scintillation counter using Aquasol-2 liquid scintillation fluid. Under these assay conditions, little or no farnesol (Rf=0.23) was formed as the result of radiolabeled FPP dephosphorylation and no further metabolism of newly-formed squalene to cholesterol (Rf=0.15) occured. In addition, under these conditions of the assay, in the absence of inhibitor, the rate of 3H release was equal to the rate of squalene formation for the overall reaction.

SQS activity (overall reaction) is calculated as pmoles of [3H] squalene formed from [1-3H] FPP per minute of incubation at 37° C. per mg microsomal protein as follows:

pmol/min/mg =

$$\frac{(DPM\ sample - DPM\ enzyme\ blank)\ (total\ assay\ volume)}{[1.5(FPP\ specific\ activity)]\ (spotted\ vol.)\ (assay\ time)\ (microsomal\ protein\ added)}$$

Example 3

105 ml of 76% butanol was added to each of the 61 flasks obtained in Example 1. The growth was manually broken with a glass pipette. The flasks were placed on a shaker at 200 rpm for 30 minutes. The flask contents were pooled. Flasks were rinsed with a small amount of butanol. The mixture was mechanically stirred and filtered. About 1500 ml of butanol was added to the cake. The cake was manually stirred and then refiltered. The mixture was divided into two parts for ease of handling. For each part 3 liters of 1% sodium bicarbonate were added to an almost equal volume of filtrate, and the mixture was shaken in a separating funnel. The bottom sodium bicarbonate layer was drawn off and the pH was lowered to 2.0 with hydrochloric acid. An equal volume of ethyl acetate was added to each of the bicarbonate layers and shaken in a separating funnel. The top ethyl acetate layers were drawn off and combined. The combined liquid was evaporated to dryness and yielded 1.747 grams of dried crude material.

On a larger volume, 10 one-liter flasks were harvested and extracted after 16 days of solid fermentation, using the same procedure as that for the 300 ml flasks mentioned above. These gave 0.55 gram of dried crude material.

The final pH of the 8 liter fermentation was 5.1. The pH was adjusted to 2.8 with 20% sulfuric acid and the whole broth was mixed well with an equal volume of ethyl acetate. It was then filtered through celite filtration aid and the mycelium re-extracted with ethyl acetate. The ethyl acetate extracts were combined and extracted with a 1% solution of sodium bicarbonate. The bicarbonate layer was acidified to pH 2.8 and reextracted with ethyl acetate. The organic layer was dried over anhydrous sodium sulfate and concentrated on a rotary evaporator to yield 7.19 gm of crude material.

Preparation of Residues A and B

The isolation procedure is represented in Scheme 1.

The crude extract was dissolved in 100 mL of methanol (MeOH) and 11 mL of water added to give a 10% aqueous methanol solution. This solution was then partitioned with an equal volume of hexanes. After the separation of the phases, water was added to the 10% aqueous methanol to give a 25% aqueous methanol solution which was then partitioned with an equal volume of toluene. The toluene layer was evaporated under reduced pressure to give residue A (5% mg). After addition of water to give a 35% aqueous methanol solution, this was partitioned with an equal volume of chloroform. Evaporation of the chloroform layer under reduced pressure gave residue B (598 mg).

Preparation of Residue C

Residues A and B which were active in the SQSI assay were combined and subjected to Sephadex LH-20 gel permeation chromatography using chloroform/methanol (1:0) solvent mixture as the eluting solvent. Twelve 10-ml fractions were collected. Activity was concentrated in fractions 5–10 which were pooled and evaporated under reduced pressure to give residue C (400 mg).

Preparative HPLC of Residue C

Examination of a sample of residue C by analytical HPLC revealed it was a complex of about seven components. Semi-preparative HPLC was therefore used to resolve this complex into its individual components.

The semi-preparative HPLC system consisted of the Waters 600E Multi-Solvent Delivery System controlled by Millennium 2010 Chromatography Manager Software, Waters Model U6K Injector, Knauer Model 87 Variable Wavelength Detector, and an HP Desk Jet Printer. The column used was a Waters RCM 25×20 cm cartridge column (segmented columns). The column was equilibrated with the mobile phase consisting of 3 parts 0.1% phosphoric acid and 7 parts acetonitrile at a flow rate of 10 mL/min. After the equilibration, a sample of residue C (200 mg in 100 μl of methyl cyanide) was injected onto the column. The HPLC separation was monitored with UV a 214 nm and peaks corresponding to the 7 components were separately collected. An additional injection of the crude mixture (200 mg) was made and similar peaks were pooled. The eluants were extracted with chloroform, dried over sodium sulfate and evaporated under reduced pressure to give solids. Fraction 4 yielded Zaragozic acid A while Fraction 5 gave a compound whose two-dimensional structure was established to be of the formula I. Fraction 6 produced a stereoisomer of the compound of Fraction 5.

SQUALENE SYNTHASE INHIBITION ASSAY (described above) RESULTS.

| Compound | IC$_{50}$ |
|---|---|
| Zaragozic acid A | 1 nM |
| Fraction 5 compound | 48 μM |

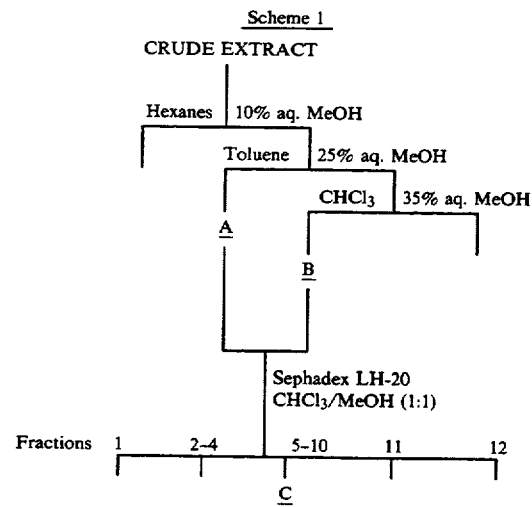

Scheme 1
CRUDE EXTRACT

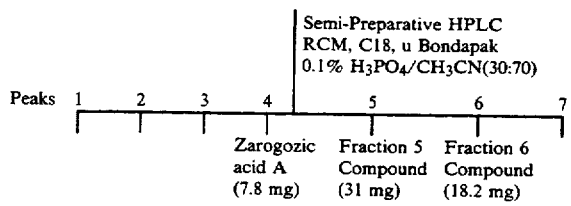

-continued
Scheme 1

PHYSICO-CHEMICAL PROPERTIES OF FRACTION 5 COMPOUND

Description: Pale-yellow solid
Molecular Formula: $C_{31}H_{38}O_{10}$
Molecular Weight: 570
Ultraviolet Spectrum: (λ max):190, 251 nm ($CH_3CN$)
Infra-Red Spectrum:
Major IR bands: 3360, 2920, 2850, 1830, 1760, 1710, 1430, 1410, 1390, 1260, 1170, 1090, 960, 930, 910, 730, 700, 640, 580 cm$^{-1}$
$^1$H NMR Spectrum: Solvent $CDCl_3$
Observed Chemical Shifts: (ppm) 5.82 (s, 1H); 5.52 (m, 1H); 5.43 (m, 1H); 5.42 (m, 1H); 5.41 (m, 1H); 4.59 (t, 1H); 4.11 (s, 1H); 3.26 (d, 1H, J=15 Hz); 2.99 (d, 1H, J=15 Hz); 2.98 (d, 1H, J=15 Hz); 2.69 (m, 2H); 2.56 (d, 1H, J=15 Hz); 2.41 (m, 1H); 2.34 (m, 2H); 2.19 (m, 1H); 1.97 (m, 1H); 1.96 (m, 2H); 1.66 (d, 3H);1.65 (d, 3H);1.61 (m, 1H);1.53 (m, 1H);1.45 (m, 1H); 1.38 (m, 1H); 1.35 (m, 2H); 1.29 (m, 1H); 1.27 (m, 1H); 1.23 (m, 1H).
$^{13}$C-NMR Spectrum: Solvent: $CDCl_3$
Observed Chemical Shifts: (ppm) 211.69 (s); 176.08 (s); 173.08 (s); 165.48 (s); 164.94 (s); 144.73 (s); 141.05 (s); 137.74 (s); 131.19 (d); 129.33 (d); 129.07 (d); 126.41 (d); 124.88 (d); 105.43 (s); 76.00 (d); 48.37 (s); 47.55 (d); 43.45 (d); 40.43 (d); 39.44 (t); 39.26 (t); 38.22 (t); 36.91 (t); 34.08 (t); 32.45 (t); 29.42 (t); 29.11 (t); 27.56 (t); 26.41 (t); 17.90 (q); 17.86 (q)

| | Analytical HPLC | |
|---|---|---|
| | System | Retention Time |
| 1. | Column: Rainin $C_{18}$, 3 μ, 4.6 × 10 mm<br>Mobile Phase: 0.1% $H_3PO_4$/$CH_3CN$ (30:70)<br>Flow Rate: 0.5 mL/min | 5.2 min |
| 2. | Column: Rainin $C_{18}$, 3 μ, 4.6 × 10 mm<br>Mobile Phase: 0.1% $H_3PO_4$/$CH_3CN$ (40:60)<br>Flow Rate: 0.5 mL/min | 10.2 min |

PHYSICO-CHEMICAL PROPERTIES OF FRACTION 6 COMPOUND

Description: Pale-yellow solid
Molecular Formula: $C_{31}H_{38}O_{10}$
Molecular Weigh: 570
Ultraviolet Spectrum: (λ max):190, 248 nm ($CH_3CN$)
Infra-Red Spectrum: KBr pellet
Major IR bands: 3332, 2930, 2856, 1769, 1717, 1438, 1415, 1356, 1265, 1217, 1173, 1137, 1064, 996, 969, 952, 931,854, 813, 772, 710, 653, 621,580 cm$^-$
$^1$H NMR Spectrum: Solvent: $CDCl_3$
Observed Chemical Shifts: (ppm) 5.65 (d, 1H); 5.48 (m, 1H); 5.41 (m, 1H); 5.40 (m, 1H); 5.38 (m, 1H); 4.56 (t, 1H); 3.53 (s, 1H); 3.29 (d, 1H, J=17 Hz); 3.06 (d, 1H, J=17 Hz); 2.95 (d, 1H, J=17 Hz); 2.71 (d, 1H, J=17

Hz); 2.66 (t, 2H); 2.58 (m, 1H); 2.34 (m, 2H); 2.30 (m, 1H); 2.28 (m, 2H); 2.06 (m, 1H); 1.96 (m, 2H); 1.64 (d, 3H); 1.64 (d, 3H); 1.64 (d, 3H); 1.30 (m, 2H); 1.27 (m, 2H); 1.25 (m, 2H); 1.20 (m, 1H).

13C-NMR Spectrum: Solvent: CDCl3
Observed Chemical Shifts: (ppm) 207.60 (s); 175.29 (s); 173.75 (s); 164.28 (s); 141.52 (s); 139.77 (s); 131.01 (d); 131.19 (d); 129.27 (d); 129.25 (d); 126.17 (d); 125.02 (d); 104.84 (s); 75.12 (d); 47.28 (s); 43.19 (s); 43.18 (d); 40.21 (t); 38.26 (t); 37.25 (t); 36.07 (t); 35.42 (d); 35.21 (t); 32.32 (t); 29.27 (t); 28.90 (t); 26.77 (t); 26.02 (t); 17.96 (t); 17.89 (q).

| Analytical HPLC | |
|---|---|
| System | Retention Time |
| 1. Column: Rainin C18, 3 μ, 4.6 × 10 mm<br>Mobile Phase: 0.1% H3PO4/CH3CN (30:70)<br>Flow Rate: 0.5 mL/min | 8.6 min |
| 2. Column: Rainin C18, 3 μ, 4.6 × 10 mm<br>Mobile Phase: 0.1% H3PO4/CH3CN (40:60)<br>Flow Rate: 0.5 mL/min | 20.2 min |

Example 4 ras Farnesyltransferase inhibition assay

The ras farnesyltransferase inhibition assay was conducted in a final volume of 25 μL. The reaction is initiated by addition of 10 μpL of the diluted rat brain cytosol to a mixture of 15 μL of the ras farnesyltransferase substrate/cofactor solution and 0.3 μL of test compound solution as set out in Table 7.

The rat brain cytosols were diluted to a protein concentration of 3.0 mg/mL. Test compound solutions were prepared in dimethyl sulfoxide at concentrations of 25 mM (final assay concentration 300 μM). Control incubations received 0.3 μL of dimethyl sulfoxide and enzyme blanks received 10 μL rat brain homogenization buffer (50 mM tris HCl (pH=7.5), 5 mM dithiothreitol, 0.2M KCl, 20 μM ZnCl2). After a 30 minute incubation at 37° C., the reaction was terminated by addition of 200 μL of 10% (v/v) HCl in EtOH. After an additional 15 minute incubation at 37° C., 300 μl absolute EtOH were added and the entire sample was applied to a filtration well of a Packard Unifilter-GF/B 96-well plate under vacuum. After complete sample addition, the filter well was washed four times with 500 μl each of absolute ethanol and allowed to dry. The bottom of the Unifilter-GF/B plate was then sealed, 50 μl Microscint-20 liquid scintillation fluid were added to each well and the plate was heat-sealed and then counted in a Packard Top-Count liquid scintillation counter.

The results of the assay are set out in Table 8.

TABLE 7

| ras Farnesyltransferase Assay | |
|---|---|
| | final assay concentrations |
| rat brain cytosolic protein | 25 μg |
| tris (pH = 7.5) | 50 Mm |
| MgCl2 | 5 mM |
| ZnCl2 | 20 μM |
| H-ras | 4 μM |
| dithiothreitol | 5 mM |
| KCl | 80 mM |
| DMSO | 1.2% |
| [1-3H]Farnesyl pyrophosphate | 0.5 μM |

TABLE 8

| Ras Farnesyltransferase Inibition Assay | |
|---|---|
| Compound | IC50 |
| Zaragozic Acid | 3 μM |
| Fraction 5 Compound | 6 μM |
| Fraction 6 Compound | 6 μM |

We claim:

1. A compound of the following chemical formula:

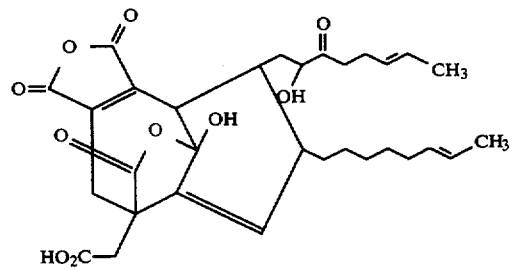

or the pharmaceutically acceptable acid addition salts thereof.

2. A composition for the treatment of fungal infections and inhibition of squalene synthase and protein farnesyltransferase comprising a compound according to claim 1 or a pharmaceutically acceptable base addition salt thereof in an amount effective in such treatments and a pharmaceutically acceptable carrier.

* * * * *